United States Patent
VanDeripe

(10) Patent No.: US 7,661,424 B2
(45) Date of Patent: *Feb. 16, 2010

(54) METHOD OF USE OF GAS MIXTURES TO ACHIEVE NITROGEN WASHOUT FROM THE BODY AND MITOCHONDRIA OF THE HEART

(75) Inventor: Donald Ray VanDeripe, Dardenne Prairie, MO (US)

(73) Assignee: Donald R. VanDeripe Revocable Trust, Dardenne Prairie, MO (US)

(*) Notice: Subject to any disclaimer, the term of this patent is extended or adjusted under 35 U.S.C. 154(b) by 96 days.

This patent is subject to a terminal disclaimer.

(21) Appl. No.: 11/827,969

(22) Filed: Jul. 16, 2007

(65) Prior Publication Data

US 2007/0277822 A1 Dec. 6, 2007

Related U.S. Application Data

(63) Continuation-in-part of application No. 10/678,379, filed on Oct. 6, 2003, now Pat. No. 7,263,993, which is a continuation-in-part of application No. 10/347,553, filed on Jan. 21, 2003, now abandoned.

(51) Int. Cl.
*A61M 16/00* (2006.01)
(52) U.S. Cl. .............................. 128/200.24; 128/204.18
(58) Field of Classification Search ............ 128/200.24, 128/203.12, 204.18, 205.11; 424/9.3
See application file for complete search history.

(56) References Cited

U.S. PATENT DOCUMENTS

| 6,001,332 A | 12/1999 | Garrett |
| 6,899,103 B1 | 5/2005 | Hood et al. |
| 6,983,749 B2 | 1/2006 | Kumar et al. |
| 7,263,993 B2 * | 9/2007 | VanDeripe ............. 128/200.24 |

OTHER PUBLICATIONS

Donald R. Vanderipe Gas Microbubbles in Biology: Their Relevance in Histology, Toxicology, Physiology and Anethesia Toxicology Methods 11: 107-126, (2001).
Donald R. Vanderipe The swelling of mitochondria from nitrogen gas; a possible cause of reperfusion damage Medical Hypotheses 62: 294-296 (2004).
Pan, Yi et al. Heliox and oxygen reduce infarct volume in a rat model of focal ischemia Exp. Neurol 205: 587-90 (2007).
Wade, CE et al. Absence of antiarrhythmic effects of helium in patients with spontaneous premature vantricular beats at rest Undersea Biomed Res. 6: 313-8 (1979).
Pifarre, MD. et al. Effect of oxygen and helium mixtures on ventricular fibrillation The Journal of Thoracic and Cardiovascular Surgery 60: 648-652 (1970).

* cited by examiner

*Primary Examiner*—Steven O Douglas

(57) ABSTRACT

The disclosure details methods and gas mixtures which are useful for washing nitrogen out of the body and mitochondria following acute cerebrovascular accidents (strokes) or myocardial infarction (heart attacks) and allow the reuptake of oxygen into mitochondria of ischemic tissues following reflow, thereby reducing the severity of reperfusion damage and cell death.

6 Claims, No Drawings

US 7,661,424 B2

METHOD OF USE OF GAS MIXTURES TO ACHIEVE NITROGEN WASHOUT FROM THE BODY AND MITOCHONDRIA OF THE HEART

CROSS REFERENCE TO RELATED APPLICATIONS

This application is a Continuation-in-Part of patent application Ser. No.10/678,379 filed on Oct. 6, 2003, now U.S. Pat. No. 7,263,993 now allowable, which was a Continuation-in-Part of patent application Ser. No. 10/347,553 filed on Jan. 21, 2003, now abandoned.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

There has been voluminous research conducted on the biochemistry of injury and disease conditions. Conversely, there has been little or no research directed at possible adverse reactions to inhaled atmospheric gases. Specifically, outside of its known potential for adverse reactions in deep sea diving, no knowledge has been developed about any undesirable reactions to inhaled nitrogen. Based on the research of the inventor, VanDeripe, Toxicology Methods 11:107-126 (2001), it becomes clear that gases other than oxygen can enter and fill mitochondria, and since these gases are not usable for oxidative metabolism, they might be expected to interfere with the production of ATP and therein compromise mitochondrial membrane integrity. Whereas this phenomenon might be expected with volatile anesthetics, what is discovered in this invention is the very real potential danger from constantly inhaled atmospheric nitrogen gas in selected injury and disease conditions. To counter these adverse effects, the instant invention proposes the use of total body nitrogen washout methodology which involves the inhalation of nitrogen-free gas mixtures composed of oxygen and helium: see VanDeripe, Medical Hypotheses 62: 294-6 (2004). Disclosures of the use of helium and oxygen on the treatment of strokes and heart attacks include U.S. Pat. No. 6,001,332 (Garrett), U.S. Pat. No. 6,899,103 (Hood et al) and U.S. Pat. No. 6,983,749 (Kumar et al.), but they clearly involve different parameters and mechanisms of action. Garrett anecdotally notes anti-arrhythmic activity for helium-oxygen mixtures in acute myocardial infarction, but without further discussion or explanation. Conversely, Wade, et al. report an absence of anti-arrhythmic activity in patients with spontaneous premature ventricular beats; see Undersea Biomed. Res. 6:313-8 (1979). Piffare, et al. The Journal of Thoracic and Cardiovascular Surg. 60:648-52 (1970) noted short term ant-arrhythmic activity for inhaled oxygen-helium mixtures in an animal model of permanent coronary artery dissection, but highly effective mixtures also contained air (nitrogen). Like Pifarre, Hood and Kumar also allow the admixture of air and or nitrogen to the inhaled gases, contrary to the nitrogen-free gas mixtures of this invention. Kumar, et al. use helium oxygen gas mixtures in hypothermia technology to decrease the metabolism of the entire body. Conversely, the object of this invention is to increase the metabolism in ischemic mitochondria of the myocardium. An experimental study employing the technology of this invention has been reported in a rat stroke model: see Pan, et al. Exp. Neurol. 205: 587-90 (2007).

BRIEF SUMMARY OF THE INVENTION

In certain conditions wherein blood flow may be minimally compromised or completely occluded for a period of time, the supply of oxygen to the affected tissue is decreased to a degree that some of the mitochondria in the immediate region are inadequately oxygenated. In this case, oxidative metabolism will be impaired, perhaps to a degree that mitochondrial membrane integrity is compromised and nitrogen begins to leak into and fill the intramitochondrial space. Mitochondria filled with nitrogen are unable to carry on aerobic metabolism and will develop acidosis, followed by cell death. If full reperfusion of the tissues is accomplished, one might expect the problem to reverse itself. However, since the body water of a living animal is completely saturated with nitrogen from inhaled atmospheric gases, there is no possibility for a rapid gradient reversal and washout of nitrogen from the oxygen-compromised mitochondria, so the affected tissues may proceed to cell death and necrosis. The only way to circumvent this problem of gas physics is to purge or washout nitrogen from the body tissues including the mitochondria so that oxygen can regain access to the interior of affected mitochondria. The scenario then becomes a simple matter of eliminating nitrogen from the inhaled gas mixtures and replacing it with a gas or gases which will facilitate nitrogen washout. A major total body lowering of nitrogen gas tension in normally perfused tissues will, once reperfusion is achieved, permit a rapid reverse gradient washout of nitrogen from the ischemic tissues and mitochondria. This invention describes procedures and suitable gas mixtures for use in this regard. The use of oxygen-helium gas mixtures, when inhaled as soon as possible after the onset of stroke or heart attack, can be used to effect a washout of nitrogen from the body to a degree that when reperfusion is established, nitrogen will be cleared from the ischemic tissues and oxidative metabolism will return. It is expected that the clinical benefit will be a significant reduction in reperfusion damage and cell death in the ischemic regions of strokes and heart attacks. The gas formulations for this use would include helium and oxygen at complimentary concentration ranges of 0-80% and 20-100% respectively. For purposes of this disclosure, the terms nitrogen, oxygen and helium used herein shall mean the molecular gas forms of these chemical elements.

DETAILED DESCRIPTION OF THE INVENTION

Nitrogen is a gas which comprises 79% of the air breathed by all animals. The possibility of asphyxiation from nitrogen has long been appreciated, but it has not been considered a problem so long as the inhaled oxygen concentration is 20% or higher. Although nitrogen is generally a benign carrier gas, there are conditions wherein it can become toxic even in the presence of normal or elevated (20-100%) concentrations of inhaled oxygen. In those instances wherein nitrogen enters and partially or completely fills the intramitochondrial space, it can physically block oxygen uptake leading to anaerobic metabolism, acidosis and cell death. In clinical medicine there are some specific conditions in which nitrogen toxicity becomes a problem when blood flow to organs or tissues is blocked, i.e. cerebrovascular accidents (strokes), or myocardial infarctions (heart attacks), among others. Following these incidents, mitochondria in the blood flow compromised regions continue to utilize oxygen from the immediate aqueous environment, but when that supply is exhausted the affected mitochondria cease oxidative metabolism leading to a reduction in the production of ATP and a breakdown of mitochondrial membrane integrity. At this point nitrogen begins to leak into and fill the mitochondria A subsequent replenishment of blood flow is often less than successful in providing full re-oxygenation and metabolic recovery to the tissue, because that nitrogen entrapped within the mitochondria physically blocks the re-entry of oxygen. This may explain the phenomenon known as 'luxury perfusion', wherein the tissues sometimes fail to recover following reperfusion even though bathed by an apparent excess of blood and oxygen. The need for improved medical therapy for strokes and heart attacks is clear. It is this inventors carefully studied scientific conclusion that strokes and heart attacks can be favorably treated by inhaling various gas formulations which foster the washout of nitrogen from the body and mitochondria, allow the re-entry of oxygen into mitochondria and re-establish oxidative metabolism. The number of effective formulations might be many, but for the purposes of this invention would be limited to mixtures of oxygen and helium. Any gas formulation which has as its main purpose the washout of nitrogen from the body would surely be devoid of nitrogen per se. Oxygen would be a requisite gas and could be used at a concentration of 100%, but that might not foster the fastest washout of nitrogen from the body and mitochondria. The oxygen content of the inhaled mixtures would be established at a range of about 20-100%. Helium is very desirable because of its low density. Indeed, it has been used in conjunction with oxygen as a gas mixture (heliox) to promote ease of breathing for patients with impaired respiratory function. Helium could find high penetrability into mitochondria and facilitate the washout of nitrogen. Although helium is expensive its low solubility would only require about 700ml for saturation of the body water. Therefore, helium would be employed at concentrations as low as 0% ranging up to 80%, i.e. complimentary to oxygen to achieve the total of 100%. The specific concentrations of the two gases within the ranges specified above would not be as important as the exclusion of nitrogen from the mixture and the specific nitrogen washout technique described below. In practical clinical use, an optimized mixture of oxygen and helium would be inhaled from a suitable gas delivery system such as premixed tanks, tanks with mixing valves or hospital gas supply lines, and exhaled gases would be shunted to the ambient atmosphere through a one-way flutter valve. Typically the heart attack or stroke patient would inhale an optimized mixture of oxygen and helium with exhaled gases shunted to ambient atmosphere to force the washout of nitrogen from the body.

This nitrogen washout technique could be started during patient transport or upon admission to the hospital. Nitrogen would be washed out of the body at a rate of about 18 ml per minute so that so that about half (50%) of the body nitrogen would be exhaled during the first half hour. This washout estimate is based on pro forma calculations of about 70 liters of body water and a 1.5% water solubility for nitrogen, which calculates to 1050 ml as the saturated total body water capacity for nitrogen; and 18 ml for 30 minutes calculates to 540 ml, i.e. about half of the total body water nitrogen. If 50% can be projected as the minimum percentage washout which would provide any significant clinical benefit, improved clinical results might be expected from nitrogen washouts of 75-90% or more and this could require washout periods of 60-90 minutes or longer. If, at these or some delayed time frames, blood flow is restored to the ischemic tissues, there would exist a higher concentration of nitrogen in the water and mitochondria of the ischemic region than in the surrounding tissues which had been undergoing nitrogen washout. As a result, a reverse partial pressure gradient for nitrogen would exist which would promote the removal of nitrogen from the ischemic region back into the circulating blood and to the lungs for exhalation. This reverse gradient would also extend to that nitrogen trapped in the mitochondria, and it would also be expected that the small molecule of helium would easily gain access to the interior of the affected mitochondria to further hasten the nitrogen washout. Along with helium, oxygen would then regain access into mitochondria, returning said mitochondria to a state of oxidative metabolism with a concurrent return of mitochondrial membrane integrity and selectivity.

In practice, the patient would continue to breathe that gas mixture for 30 minutes minimum up to about 72 hours depending on the severity and duration of the original vascular blockade. The extended time frame beyond 1-2 hours for inhaling the gas mixture and continuing nitrogen washout may be a clinical decision to ensure that mitochondrial metabolism and mitochondrial membrane repair, function and stability have been fully restored to levels wherein the reintroduction of high concentrations of inhaled nitrogen would not re-aggravate the ischemic injury. Clearly, in the scope of the invention, i.e. washout of nitrogen from the body and mitochondria, there are many gas mixtures which might be contemplated and which should be considered as being anticipated by this is disclosure. However, for the purposes of the specific uses mentioned above, the exhalation-facilitated washout of nitrogen process per se is paramount, and the favored gas mixtures need only contain oxygen, but most favorably, also helium.

The hardware, gas cylinder, gas mixing technology, one-way flutter valves and other ancillary equipment required to practice this invention are known in the art and are not part of this invention. Multiple systems could prove useful at various stages of the nitrogen washout process. The most effective would employ a face mask inhalation device with a one-way valve to shunt exhaled gases into the ambient atmosphere. Less effective systems, but suitable for longer periods of slower nitrogen washout or for maintenance of low concentrations of inhaled nitrogen would be bed tents or drapes with exit ports for exhaled gases, wherein some re-breathing of exhaled nitrogen would be expected. As well, nasal cannula tubing systems could be employed, but these would be open to some inhaled nitrogen gas contamination from room air. When and how best to employ the various equipment options would be determined over time through clinical use experience. This invention is restricted to the use of certain limited gas mixtures as a means of medical therapy to reverse nitrogen accumulation from normal and ischemic tissue, and in particular from mitochondria.

What is claimed is:

1. The method of inhalation of specific gas mixtures in a human being with exhaled gases being shunted into ambient atmosphere to effect a 50-90% washout of at least 50-90% of nitrogen gas from the body, body water, ischemic tissues and mitochondria in order to allow the reuptake of oxygen into hypoxic mitochondria and restore oxidative metabolism to affected tissues following reversible vascular occlusion in a myocardial infarction (heart attack), which comprises the administration of said gas mixtures from a suitable supply source and is implemented as quickly as possible following the vascular event and continued for a minimum of 30 minutes up to 72 hours to assure optimum therapy and minimize cell death, wherein the specific gas mixtures are complimentary concentrations of 20-80% of oxygen and helium respectively.

2. The method of claim 1 wherein the gas mixture is 30% oxygen and 70% helium.

3. The method of inhaling specific gas mixtures in a human being with exhaled gases being shunted into ambient atmosphere to effect a washout of at least 90% of nitrogen gas from the body, body water, ischemic tissues and mitochondria in order to allow the reuptake of oxygen into hypoxic mitochondria and restore oxidative metabolism to the affected tissues following reversible vascular occlusions in a myocardial infarction (heart attack), which comprises the administration of said gas mixtures from a suitable supply source and is implemented as quickly as possible following the vascular event and continued for 30 minutes up to 72 hours to assure optimum therapy and minimize cell death, wherein the specific gas mixtures are complimentary concentrations of 20-80% oxygen and helium respectively.

4. The method of claim 3 wherein the gas mixture is 30% oxygen and 70% helium.

5. The method of inhalation of specific gas mixtures in a human being with exhaled gases being shunted into ambient atmosphere to effect a washout of at least 90% of nitrogen gas from the body, body water, ischemic tissues and mitochondria in order to allow the reuptake of oxygen into hypoxic mitochondria and restore oxidative metabolism to affected tissues following reversible vascular occlusions in a myocardial infarction (heart attack), which comprises the administration of said gas mixtures from a suitable supply source and is implemented as quickly as possible following the vascular event and continued for a minimum of 30 minutes up to 72 hours to assure optimum therapy and minimize cell death, wherein the specific gas mixtures are complimentary concentrations of 20-80% of oxygen and helium respectively.

6. The method of claim 5 wherein the gas mixture is 30% oxygen and 70% helium.

\* \* \* \* \*

UNITED STATES PATENT AND TRADEMARK OFFICE
CERTIFICATE OF CORRECTION

PATENT NO. : 7,661,424 B2
APPLICATION NO. : 11/827969
DATED : February 16, 2010
INVENTOR(S) : Donald Ray VanDeripe It is certified that error appears in the above-identified patent and that said Letters Patent is hereby corrected as shown below:

Column 4, Claim 1: Cancelled

Column 5, Claim 2: Cancelled

Column 5, Claim 3: Cancelled

Column 6, Claim 4: Cancelled

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,661,424 B2 | Page 1 of 2 |
| APPLICATION NO. | : 11/827969 | |
| DATED | : February 16, 2010 | |
| INVENTOR(S) | : Donald Ray VanDeripe | |

It is certified that error appears in the above-identified patent and that said Letters Patent is hereby corrected as shown below:

Delete the title page and substitute therefore the attached title page showing the corrected number of claims in patent.

Column 4, line 56 - Column 6, line 2, delete claims 1-4.

Column 6, line 3 - 18, Claims 5 and 6, are to be renumbered as claims 1 and 2, and should appear as follows Claim 1. The method of inhalation of specific gas mixtures in a human being with exhaled gases being shunted into ambient atmosphere to effect a washout of at least 90% of nitrogen gas from the body, body water, ischemic tissues and mitochondria in order to allow the reuptake of oxygen into hypoxic mitochondria and restore oxidative metabolism to affected tissues following reversible vascular occlusions in a myocardial infarction (heart attack), which comprises the administration of said gas mixtures from a suitable supply source and is implemented as quickly as possible following the vascular event and continued for a minimum of 30 minutes up to 72 hours to assure optimum therapy and minimize cell death, wherein the specific gas mixtures are complimentary concentrations of 20-80% of oxygen and helium respectively.

Claim 2. The method of claim 1 wherein the gas mixture is 30% oxygen and 70% helium.

This certificate supersedes the Certificate of Correction issued May 11, 2010.

Signed and Sealed this

Twenty-second Day of June, 2010

David J. Kappos
*Director of the United States Patent and Trademark Office*

(12) United States Patent
VanDeripe

(10) Patent No.: US 7,661,424 B2
(45) Date of Patent: *Feb. 16, 2010

(54) METHOD OF USE OF GAS MIXTURES TO ACHIEVE NITROGEN WASHOUT FROM THE BODY AND MITOCHONDRIA OF THE HEART

(75) Inventor: Donald Ray VanDeripe, Dardenne Prairie, MO (US)

(73) Assignee: Donald R. VanDeripe Revocable Trust, Dardenne Prairie, MO (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/827,969

(22) Filed: Jul. 16, 2007

(65) Prior Publication Data

US 2007/0277822 A1 Dec. 6, 2007

Related U.S. Application Data

(63) Continuation-in-part of application No. 10/678,379, filed on Oct. 6, 2003, now Pat. No. 7,263,993, which is a continuation-in-part of application No. 10/347,553, filed on Jan. 21, 2003, now abandoned.

(51) Int. Cl.
*A61M 16/00* (2006.01)
(52) U.S. Cl. ................................ 128/200.24; 128/204.18
(58) Field of Classification Search ............ 128/200.24, 128/203.12, 204.18, 205.11; 424/9.3
See application file for complete search history.

(56) References Cited

U.S. PATENT DOCUMENTS

| 6,001,332 | A | 12/1999 | Garrett |
| 6,899,103 | B1 | 5/2005 | Hood et al. |
| 6,983,749 | B2 | 1/2006 | Kumar et al. |
| 7,263,993 | B2 * | 9/2007 | VanDeripe ............ 128/200.24 |

OTHER PUBLICATIONS

Donald R. Vanderipe Gas Microbubbles in Biology: Their Relevance in Histology, Toxicology, Physiology and Anethesia Toxicology Methods 11: 107-126, (2001).

Donald R. Vanderipe The swelling of mitochondria from nitrogen gas; a possible cause of reperfusion damage Medical Hypotheses 62: 294-296 (2004).

Pan, Yi et al. Heliox and oxygen reduce infarct volume in a rat model of focal ischemia Exp. Neurol 205: 587-90 (2007).

Wade, CE et al. Absence of antiarrhythmic effects of helium in patients with spontaneous premature vantricular beats at rest Undersea Biomed Res. 6: 313-8 (1979).

Pifarre, MD. et al. Effect of oxygen and helium mixtures on ventricular fibrillation The Journal of Thoracic and Cardiovascular Surgery 60: 648-652 (1970).

* cited by examiner

*Primary Examiner*—Steven O Douglas

(57) ABSTRACT

The disclosure details methods and gas mixtures which are useful for washing nitrogen out of the body and mitochondria following acute cerebrovascular accidents (strokes) or myocardial infarction (heart attacks) and allow the reuptake of oxygen into mitochondria of ischemic tissues following reflow, thereby reducing the severity of reperfusion damage and cell death.

2 Claims, No Drawings